United States Patent [19]

Totakura et al.

[11] Patent Number: 5,383,904
[45] Date of Patent: Jan. 24, 1995

[54] STIFFENED SURGICAL DEVICE

[75] Inventors: Nagabhushanam Totakura, Norwalk; Ross Muth, Brookfield, both of Conn.

[73] Assignee: United States Surgical Corporation, Norwalk, Conn.

[21] Appl. No.: 959,012

[22] Filed: Oct. 13, 1992

[51] Int. Cl.⁶ .............................................. A61L 17/00
[52] U.S. Cl. .................................................. 606/228
[58] Field of Search ................ 606/228, 229, 230, 231

[56] References Cited

U.S. PATENT DOCUMENTS

| | | | |
|---|---|---|---|
| 3,896,814 | 7/1975 | Vivien et al. | 606/229 |
| 3,997,512 | 12/1976 | Casey et al. | 606/231 |
| 4,122,129 | 10/1978 | Casey et al. | 606/228 |
| 4,549,545 | 10/1985 | Levy | 606/228 |
| 4,788,979 | 12/1988 | Jarrett et al. | 606/230 |
| 5,076,807 | 12/1991 | Bezwada et al. | 606/230 |

FOREIGN PATENT DOCUMENTS

| | | | |
|---|---|---|---|
| 1306675 | 12/1989 | Japan | 606/228 |
| 913158 | 12/1962 | United Kingdom | 606/228 |

*Primary Examiner*—Tamara L. Graysay

[57] ABSTRACT

A suture-pledget combination is improved by applying a stiffening agent to at least a portion of the suture adjacent to the pledget to decrease the probability of tangling or twisting of the suture during use.

11 Claims, 1 Drawing Sheet

STIFFENED SURGICAL DEVICE

FIELD OF THE INVENTION

This invention relates to an improved suture-pledget surgical device and more particularly, to a suture-pledget device which does not become twisted or tangled adjacent to the pledget prior to or during use.

BACKGROUND OF THE INVENTION

In various surgical procedures involving closing wounds of living tissue, it is known that a pledget or cushioning pad may be used with a suture in order to buttress the suture and inhibit the suture from cutting into the tissue. Suture pledget devices find particular application in cardio-vascular surgery, where a suture cutting through delicate vascular or arterial tissue can have serious adverse consequences to the health and welfare of the patient. Surgeons often encounter difficulty, however, when placing sutures having pledgets attached to them. Sutures generally have an inherent degree of twist or memory, so sutures often tend to become tangled or twisted adjacent to the pledget prior to and during use.

Therefore, it would be desirable to provide a suture-pledget surgical device which has little or no tendency to become tangled or twisted adjacent to the pledget prior to or during use.

SUMMARY OF THE INVENTION

In accordance with the present invention, there is provided a surgical device having a suture, a pledget attached to a central region of the suture, and a stiffening agent disposed on at least a portion of the suture adjacent to the pledget. The stiffening agent acts to stiffen a portion of the suture adjacent to the pledget in order to substantially eliminate the tendency of the suture to become tangled or twisted about the pledget. The length of stiffened suture, as measured from the suture/pledget junction, and the degree of stiffness of the stiffened suture portion can be varied as desired. The invention includes embodiments wherein both the pledget and a portion of the suture are stiffened as well as embodiments wherein only a portion of the suture is stiffened adjacent to the suture/pledget junction with the pledget substantially unstiffened. Both bioabsorbable and non-bioabsorbable materials may be used as components of the surgical device and stiffening agent.

The invention also includes a method of stiffening a portion of the suture adjacent to the pledget and the method of using the suture pledget combination of the present invention.

DESCRIPTION OF THE PREFERRED EMBODIMENTS

Figure 1:
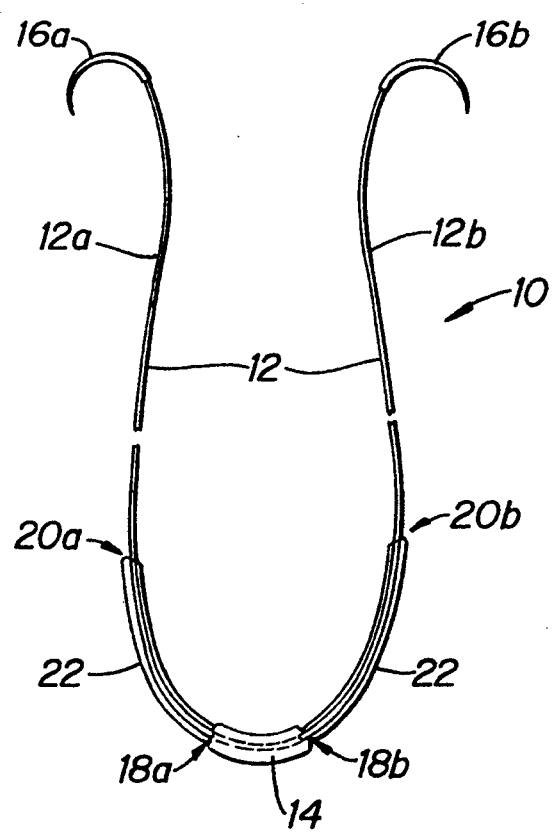
FIG. 1 is a perspective view of a needled suture with attached pledget, with a stiffened portion of the suture adjacent to the pledget.

Referring now to the drawing, in which the preferred embodiment of the present invention is illustrated. The surgical device, generally denoted by numeral 10, has suture 12, and a pledget 14 attached to a central region of suture 12. For most applications, the suture is double-armed, including needles 16a and 16b attached to each end of suture 12. Suture/pledget junctions 18a and 18b illustrate where suture 12 passes through pledget 14, with the portion of suture 12 shown in phantom disposed behind pledget 14 in order to accomplish the purpose and objective of the suture pledget combination. Suture portions 12a and 12b extend from the pledget to needles 16a and 16b, respectively. The invention includes a stiffening agent 22 disposed on at least a portion of the suture adjacent to the pledget. Numerals 20a and 20b indicate the points of transition from stiffened suture to unstiffened suture. Therefore, for example, the stiffened portion of the suture can extend towards needles 16a and 16b from suture/pledget junctions 18a and 18b, terminating at 20a and 20b.

Wounds may be sutured with the suture described herein by passing needles 16a and 16b through tissue to create wound closure. The needles preferably are then removed from the suture and the suture is tied.

In a preferred embodiment, the stiffening agent is applied to both suture 12 and pledget 14, the suture being stiffened from 0 to 100% of the suture portions 12a, 12b extending from suture/pledget junctions 18a and 18b, more preferably from about 5 to about 50% of the length of suture portions 12a and 12b, and most preferably about 10 to about 20% the length of suture portions 12a and 12b. Because suture lengths differ widely, it is convenient to refer to the length of the stiffened suture portion. Thus, stiffened suture segments can extend about 0 to 10 inches from pledget 14, more preferably about 1 to 5 inches and most preferably about 2 to 4 inches from the suture pledget junctions.

The desired degree of stiffness will also require a balancing of surgeon preference with respect to suture handling characteristics, e.g., a balancing of suture flexibility for handling against sufficient stiffness to prevent twisting or tangling. In either case, the pledget optionally can also be stiffened or the pledget may be unstiffened with only the suture being stiffened.

Suture 12 can be fabricated of either bioabsorbable polymeric resins or of non-bioabsorbable biocompatible materials. Suitable bioabsorbable polymeric resins include, for example, homopolymers and copolymers derived from members of the group consisting of polyglycolic acid, glycolide, lactide, lactic acid, dioxanone, epsiloncaprolactone, trimethylene carbonate and mixtures thereof. Polymers and copolymers of the foregoing kind and absorbable surgical devices made therefrom are well known. See, e.g., U.S. Pat. Nos. 2,668,162; 2,703,316; 2,758,987; 3,225,766; 3,297,033; 3,422,181; 3,531,561; 3,565,869; 3,620,218; 3,626,948; 3,636,956; 3,736,646; 3,772,420; 3,773,919; 3,792,010; 3,797,499; 3,839,297; 3,867,190; 3,878,284; 3,982,543; 4,060,089; 4,137,921; 4,157,437; 4,234,775; 4,237,920; 4,300,565; 4,523,591; and, 5,019,093; U.K. Patent No. 779,291; D. K. Gilding et al., "Biodegradable polymers for use in surgery -polyglycolic/poly(lactic acid) homo- and co- polymers": 1, Polymer, Volume 20, pages 1459–1464 (1979), and D. F. Williams (ed.), Biocompatibility of Clinical Implant Materials, Vol. II, ch. 9: "Biodegradable Polymers" (1981).

Examples of suitable non-bioabsorbable biocompatible materials include homopolymers and copolymers of polypropylenes. silks, polyamides, polyesters, polyvinyl chlorides, and polysulfones. Materials of the foregoing kind are well known. See, e.g., U.S. Pat. Nos. 4,911,165, 4,620,542, 4,557,264, 4,520,882, 3,630,205, 3,359,983, 3,432,514, 3,424,164, 3,130,728, 2,190,770, 2,071,253, 2,071,253. With respect to cardiovascular surgery, braided Dacron (Dupont) sutures are commonly used.

The suture may include suitable dyes, coatings, plasticizers, fillings, etc. as desired or appropriate to improve the visibility and/or handling characteristics of the suture. The stiffening agent preferably is applied after the coated or dyed suture is attached to the pledget.

Suitable pledgets 14 can also be made of bioabsorbable or non-bioabsorbable biocompatible materials. Bioabsorbable pledget materials can be selected from the group consisting of, for example, homopolymers and copolymers of polyglycolic acid, glycolide, lactide, lactic acid, dioxanone, epsilon-caprolactone, trimethylene carbonate and mixtures thereof. Examples of non-bioabsorbable biocompatible pledget materials include polyesters, polyurethane and polytetrafluoroethylene. A particularly preferred non-bioabsorbable pledget consists of TEFLON (Dupont) polytetrafluoroethylene. Examples of various methods of manufacturing these materials and, in some instances, piedgets made thereof, may be found in U.S. Pat. Nos. 2,929,800; 3,929,804; 3,428,711; 3,557,044; 4,034,850; 4,043,331; 4,044,404; 4,127,124; 4,164,046; and 4,549,545.

Suitable stiffening agents are biocompatible materials capable of stiffening the suture sufficiently to substantially eliminate tangling or twisting of suture positions 12a and 12b upon each other adjacent to pledget 14. Such stiffening agents are preferably liquid or liquid soluble for ease of application to the surgical device, and may be either bioabsorbable or non-bioabsorbable. Examples of such stiffening agents include homopolymers and copolymers of vinyl alcohol, hydroxy alkyl methacrylate, acrylamide, n-vinyl pyrrolidone, alkylene oxide and mixtures thereof. Of this group, poly (2-hydroxyethyl methacrylate) is preferred. Poly (2-hydroxyethyl methacrylate) can be dissolved in an organic solvent, such as ethyl alcohol. Other suitable stiffening agents include carboxyalkyl cellulose, aliginic acid, poly-n-acetyl glucose amine, gelatin, collagen, hyaluronic acids and mixtures and copolymers thereof. These stiffening agents may be water soluble. All stiffening agents are preferably those having no appreciable toxicity for the body when present at the levels present sufficient to obtain the desired degree of stiffening.

To be suitable, for applying a stiffening agent to the suture, a solvent must (1) be miscible with the stiffening agent at a suitable concentration of stiffening agent, (2) have a sufficiently high vapor pressure to be readily removed by evaporation, (3) not appreciably affect the integrity of the pledget and/or suture and (4) capable, in combination with the stiffening agent, of wetting the surface of the pledget and/or suture.

Application of the stiffening agent to the pledget and/or suture can be carried out in any number of ways. Thus, for example, the suture and/or pledget and suture can be submerged in the stiffening agent or solution thereof until a suitable quantity of stiffening agent sufficient to obtain the desired stiffening is acquired or otherwise retained by the suture and/or pledget after removal of any excess agent and/or accompanying solvent, if any, such as by drainage, wiping, evaporation, etc. In many cases, contact times on the order of from just a few seconds, e.g., about 2 to about 50 seconds to several minutes or hours, e.g., about 2 to about 50 minutes or about 1 to about 2 hours and even longer, are sufficient to impart the desired degree of stiffness to reduce tangling or twisting of the suture adjacent to the pledger, as compared with the same type of surgical article which has not been treated with a stiffening agent. To prevent the pledget from being stiffened, the pledget can be covered with a material capable of preventing the stiffening agent from contacting the pledget. Examples of suitable pledget covering materials are any materials resistant to the stiffening agent and any associated solvent and include metal foils, e.g. aluminum foil which can be tightly wrapped around the pledget during immersion of the suture and pledget into a stiffening agent mixture.

Alternatively, the stiffening agent and solutions thereof can be applied by coating, spraying, brushing, etc., on the surfaces of the surgical device such that the latter receives and retains a sufficient quantity of the stiffening agent to decrease the probability of tangling or twisting thereof. It may be advantageous to perform one or more applications of the stiffening agent where particular functional properties are desired.

While the surgical devices of the present invention are generally useful for retaining living tissue in a desired relationship during a healing process by positioning and emplacing living tissue therewith, such devices are also useful for the closing of wounds of living tissue by sewing together the edges thereof using conventional suturing techniques.

In order that those skilled in the art may be better able to practice the present invention, the following examples are given as illustrations of the preparation of a surgical device of the present invention. It should be noted that the invention is not limited to the specific details embodied in the examples.

EXAMPLE I

A solution of 95% ethyl alcohol and 5% distilled water were mixed well. About 25 grams of poly (2-hydroxyethyl methacrylate) were dissolved in about 100 grams of the above ethyl alcohol/water solution and stirred slowly until the solution clears. A size 2/0 DACRON polyester suture (SURGIDAC, United States Surgical Corporation, Norwalk Conn.) having a non-absorbable Teflon pledget was submerged into the solution such that the pledget was completely submerged and a portion of the suture was submerged such that the stiffening solution contacted about one inch of the suture on either side of the suture/pledget junction. Submersion time was approximately 20 seconds. Upon removal, excess stiffening solution was allowed to drip off. The surgical device was then allowed to dry under ambient conditions. The resulting suture-pledget device exhibited sufficient stiffness of the suture adjacent to the pledget to prevent twisting and tangling of the suture adjacent to the pledget. Advantageously, the suture pledget device also exhibited favorable handling characteristics for a surgeon's use.

EXAMPLE II

A stiffening solution of 5% gelatin in deionized water was prepared by adding 5 grams of gelatin (150 bone, Kind & Knox, a division of Knox Gelatin, Inc.). The solution was stirred and warmed to about 60° C. until the solution cleared. A pledget, centrally located on a SURGIDAC 2-0 (United States Surgical Corporation, Norwalk Conn.) suture, was covered with aluminum foil to prevent contact between the pledget and stiffening solution. The covered pledget and suture were submersed in the stiffening solution for approximately 20 seconds such that approximately one inch of suture to either side of the pledget were contacted and were coated with stiffening solution. Upon removal, excess stiffening solution was allowed to drip off. The surgical device then was allowed to dry under ambient conditions after which the aluminum foil covering the pledget was removed.

Although the illustrative embodiments of the present invention have been described herein with reference to the accompanying drawing, it is to be understood that the invention is not limited to those precise embodiments, and that various other changes and modifications may be affected therein by one skilled in the art without departing from the scope or spirit of the invention.

What is claimed is:

1. A method of treating a suture-pledget device with a pledget disposed on a central region of the suture comprising applying a stiffening agent to at least a portion of the suture adjacent to the pledget wherein the stiffening agent is applied to the suture and the pledget is substantially unstiffened.

2. The method according to claim 1 wherein said step of applying a stiffening agent comprises submerging at least a portion of the suture in the stiffening agent.

3. The method according to claim 1 wherein the step of applying a stiffening agent comprises coating, spraying, brushing or wiping the stiffening agent onto at least a portion of the suture.

4. The method according to claim 1 further comprising covering the pledge with a material suitable for preventing the stiffening agent from contacting said pledget.

5. The method according to claim 4 wherein the material covering the pledget is a metal foil.

6. The method according to claim 1 wherein the stiffening agent comprises homopolymers and copolymers selected from the group consisting of polyvinyl alcohol, polyhydroxy alkyl methacrylate, polyacrylamide, polyalkylene oxide and mixtures thereof.

7. The method according to claim 6, wherein the stiffening agent comprises poly (2-hydroxyethylmethacrylate).

8. The method according to claim 6, wherein the step of applying a stiffening agent comprises applying to the suture a solution of stiffening agent dissolved in at least one organic solvent.

9. The method according to claim 7, wherein the organic solvent is ethyl alcohol.

10. The method according to claim 1 wherein the stiffening agent comprises materials selected from the group consisting of carboxymethyl cellulose, alginic acid, poly-n-acetyl glucose amine, poly-n-vinyl-2-pyrrolidone, and mixtures and copolymers thereof.

11. The method according to claim 10 wherein the solvent is water.

* * * * *